United States Patent
Baker et al.

(10) Patent No.: US 10,898,460 B1
(45) Date of Patent: Jan. 26, 2021

(54) LEISHMANIA INHIBITORS

(71) Applicants: Bill J. Baker, Temple Terrace, FL (US);
Nerida G. Wilson, Cottesloe (AU);
Dennis E. Kyle, Tampa, FL (US);
Anne-Claire D. Limon, Tampa, FL (US)

(72) Inventors: Bill J. Baker, Temple Terrace, FL (US);
Nerida G. Wilson, Cottesloe (AU);
Dennis E. Kyle, Tampa, FL (US);
Anne-Claire D. Limon, Tampa, FL (US)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 16/417,117

(22) Filed: May 20, 2019

Related U.S. Application Data (60) Provisional application No. 62/701,383, filed on Jul. 20, 2018.

(51) Int. Cl.
| | |
|---|---|
| *A61K 31/343* | (2006.01) |
| *A61P 33/02* | (2006.01) |
| *A61K 31/05* | (2006.01) |
| *A61K 31/194* | (2006.01) |
| *A61K 31/122* | (2006.01) |
| *A61K 31/575* | (2006.01) |

(52) U.S. Cl.
CPC ........... *A61K 31/343* (2013.01); *A61K 31/05* (2013.01); *A61K 31/122* (2013.01); *A61K 31/194* (2013.01); *A61K 31/575* (2013.01); *A61P 33/02* (2018.01)

(58) Field of Classification Search
CPC .... A61K 31/343; A61K 31/05; A61K 31/122; A61K 31/194; A61K 31/575; A61P 33/02
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,687,666 A | 8/1987 | O'Daly |
| 4,938,949 A | 7/1990 | Borch |
| 4,992,478 A | 2/1991 | Geria |
| 5,167,649 A | 12/1992 | Zook |
| 6,638,517 B2 | 10/2003 | Reed et al. |
| 6,960,648 B2 | 11/2005 | Bonny |
| 2002/0035243 A1 | 3/2002 | Imfeld |
| 2002/0120100 A1 | 8/2002 | Bonny |
| 2003/0032594 A1 | 2/2003 | Bonny |
| 2004/0170636 A1 | 9/2004 | Matlashewski |
| 2008/0241193 A1 | 10/2008 | Fisher |

FOREIGN PATENT DOCUMENTS

| | | |
|---|---|---|
| EP | 0293827 A2 | 12/1988 |

OTHER PUBLICATIONS

Palermo et al (J.Org.Chem 2000, 65, 4482-4486).*

* cited by examiner

*Primary Examiner* — Savitha M Rao
(74) *Attorney, Agent, or Firm* — Meunier Carlin & Curfman LLC (57) ABSTRACT

In one aspect, methods and compositions for treating parasitic diseases, for example, leishmaniasis.

18 Claims, 4 Drawing Sheets

LEISHMANIA INHIBITORS

CROSS REFERENCE TO RELATED APPLICATIONS

This application claims the benefit of U.S. Provisional Patent Application Ser. No. 62/701,383 filed Jul. 20, 2018, the disclosure of which is expressly incorporated herein by reference.

STATEMENT REGARDING FEDERALLY SPONSORED RESEARCH OR DEVELOPMENT

This invention was made with Government Support under Grant Nos. PLR-1341339, ANT-1043749, and ANT-0838776 awarded by the National Science Foundation; and Grant No. R21 AL103673 awarded by the National Institutes of Health. The Government has certain rights in the invention.

FIELD

The subject matter disclosed herein generally relates to compositions and methods for treating a subject with a parasitic disease, particularly parasitic disease caused by *Leishmania* sp.

BACKGROUND

Leishmaniasis is a protozoan vector borne parasitic disease caused by protozoan parasites of the genus *Leishmania* and is transmitted through the bite of certain species of Phlembotominae sandfly. Of the approximately 30 species of *Leishmania* known to infect mammals, 21 of these species are believed to cause leishmaniasis in humans. Leishmaniasis has been reported on all continents except Australia and *Antarctica*, and has been found in parts of about 88 countries. Leishmaniasis is primarily a disease of the developing countries, and is rarer in the developed world. However, cases have been reported in military personnel who have served in the Persian Gulf. In the Americas, leishmaniasis can be found in Mexico and South America, but has recently been shown to be spreading to Texas.

Leishmaniasis manifests in three distinct forms including; cutaneous leishmaniasis (CL), visceral leishmaniasis (VL) and mucocutaneous leishmaniasis (ML). Of the three variants recognized by the Centers for Disease Control and Prevention (CDC), CL and VL are considered endemic diseases in tropical and subtropical regions throughout the world. Leishmaniasis threatens approximately 350 million humans in nearly 90 countries. Currently, approximately 12 million humans are believed to be infected, with over 2 million new cases being reported each year. Leishmaniasis disproportionately affects the poorest inhabitants of the world and significantly hinders the economic development of these developing societies.

Due to the complex life cycles of the causative parasites, leishmaniasis is rarely diagnosed in its early stages when therapeutic intervention is most effective. Leishmaniasis typically presents as skin sores or ulcers which erupt weeks to months after the person is bitten. However, if left untreated, the infection can progress and lead to splenomegaly, liver damage, renal damage, anemia, and death.

Therapeutic compounds containing antimony, specifically pentavalent antimonials (e.g., meglumine antimonate and sodium stibogluconate) were the first drugs introduced to treat leishmaniasis, and they remain the first-line therapeutic approach in many parts of the world. However, use of pentavalent antimonials is associated with significant adverse effects and are administered by intravenous or intramuscular injection. Moreover, the use of these drugs as first-line therapy for over 50 years has resulted in the emergence of drug-resistant parasites.

Unfortunately, despite the significant prevalence of this disease throughout large portions of the world, there remains a scarcity of therapeutic agents that have potent activity against *Leishmania* species with minimal adverse effect on the patient and an efficient route of administration. Therefore, there remains a need for methods and compositions that overcome these deficiencies and that provide a therapeutic alternative for leishmaniasis.

SUMMARY

Compositions and methods for treating a subject for a parasitic disease are disclosed herein. The composition can be a pharmaceutical composition comprising a therapeutically effective amount of a compound, or a pharmaceutically acceptable derivative thereof, and a pharmaceutically acceptable carrier, wherein the compound has a structure represented by formula (I) or formula (II):

wherein $R_1$, $R_2$, and $R_5$ are independently selected from hydrogen, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine;

$R_{1a}$, $R_{1b}$, $R_{2a}$, and $R_{10}$ are independently selected from hydrogen, hydroxyl, amine, halogen, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine;

$R_3$ and $R_4$ are independently, for each occurrence, selected from hydrogen, hydroxyl, substituted or unsubstituted $C_1$-$C_6$ alkyl, substituted or unsubstituted $C_1$-$C_6$ ester, or $R_3$ and $R_4$ combine together with the atom to which they are attached to form a carbonyl;

$R_{3a}$ and $R_{4a}$ are independently selected from hydrogen, hydroxyl, substituted or unsubstituted $C_1$-$C_{10}$ alkyl, substituted or unsubstituted $C_1$-$C_{10}$ alkenyl, substituted or unsubstituted $C_1$-$C_{10}$ ester, or $R_{3a}$ and $R_{4a}$ combine together with the atoms to which they are attached to form a carbonyl;

$R_6$ is selected from hydrogen, hydroxyl, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine;

$R_7$ and $R_{7a}$ are independently selected from hydrogen, hydroxyl, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine; or $R_6$ and $R_7$ combine together with the atoms to which they are attached form a substituted or unsubstituted $C_5$-$C_8$cycloalkyl, a substituted or unsubstituted $C_5$-$C_8$ cycloalkenyl, or a substituted or unsubstituted $C_5$-$C_8$ heterocycle;

$R_9$ and $R_{11}$ are independently selected from hydrogen, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine; and $R_{12}$ is selected from hydrogen, hydroxyl, amine, halogen, cyano, nitro, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine; and ---- represents a bond that is present or absent.

The method of treating an infection can comprise delivering to a subject in need thereof, a pharmaceutical composition, wherein the pharmaceutical composition comprises a therapeutically effective amount of a compound, or a pharmaceutically acceptable derivative of the compound, and a pharmaceutically acceptable carrier, to treat the infection. In some aspects of the methods described herein, the infection can be a parasitic infection. For example, the parasitic infection can be associated with a *Leishmania* sp. such as *Leishmania donovani*.

DETAILED DESCRIPTION

The compositions and methods described herein may be understood more readily by reference to the following detailed description of specific aspects of the disclosed subject matter.

Before the present compositions and methods are disclosed and described in detail, it is to be understood that the aspects described below are not limited to specific microbiota composition, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the transplant" includes mixtures of two or more such transplants, and the like.

"Optional" or "optionally" means that the subsequently described event or circumstance can or cannot occur, and that the description includes instances where the event or circumstance occurs and instances where it does not.

The term "subject" refers to any individual who is the target of administration or treatment. The subject can be a vertebrate, for example, a mammal. Thus, the subject can be a human or veterinary patient. In some embodiments, the subject is a human. The term "patient" refers to a subject under the treatment of a clinician, e.g., physician.

The term "disease" refers to a state of health of a subject wherein the subject cannot maintain homeostasis, and wherein if the disease is not ameliorated then the subject's health continues to deteriorate. The term "disorder" refers to a state of health in which the subject is able to maintain homeostasis, but in which the subject's state of health is less favorable than it would be in the absence of the disorder.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Example substituents may include halogen, hydroxy, alkyl, alkoxy, nitro, nitrate ester, ester, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(═O)Rb, —NRaC(═O)NRaNRb, —NRaC(═O)ORb, —NRaSO$_2$Rb, —C(═O)Ra, —C(═O)ORa, —C(═O)NRaRb, —OC(═O)NRaRb, —ORa, —SRa, —SORa, —S(═O)$_2$Ra, —OS(═O)$_2$Ra and —S(═O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols A″ is used herein as merely a generic substituent in the definitions below.

The term "alkoxy" as used herein is an alkyl group bound through a single, terminal ether linkage; that is, an "alkoxy" group can be defined as —OA$^1$ where A$^1$ is alkyl as defined above.

The term "alkenyl" as used herein is a hydrocarbon group of from 2 to 24 carbon atoms with a structural formula containing at least one carbon-carbon double bond. Asymmetric structures such as (A$^1$A$^2$)C═C(A$^3$A$^4$) are intended to include both the E and Z isomers. This may be presumed in structural formulae herein wherein an asymmetric alkene is present, or it may be explicitly indicated by the bond symbol C═C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O⁻.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the halogens fluorine, chlorine, bromine, and iodine.

The term "hydroxyl" as used herein is represented by the formula —OH.

The term "nitro" as used herein is represented by the formula —NO$_2$.

The term "cyano" as used herein is represented by the formula —CN.

The term "sulfonyl" is used herein to refer to the sulfo-oxo group represented by the formula —S(O)$_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH$_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable derivative" or "pharmaceutically acceptable salt" refers to a salt that is pharmaceutically acceptable and has the desired pharmacological properties. Such derivatives or salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Reference will now be made in detail to specific aspects of the disclosed materials, compounds, compositions, articles, and methods, examples of which are illustrated in the accompanying Examples.

Compounds

Disclosed herein are compounds that can be used to treat infectious diseases. The compounds described herein can be an alcyopterosin or an oxidized steroid. In some embodiments, the compounds can have structures represented by formula (I) below:

(I)

wherein $R_1$, $R_2$, and $R_5$ are independently selected from hydrogen, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine;

$R_3$ and $R_4$ are independently, for each occurrence, selected from hydrogen, hydroxyl, substituted or unsubstituted $C_1$-$C_6$ alkyl, substituted or unsubstituted $C_1$-$C_6$ ester, or $R_3$ and $R_4$ combine together with the atom to which they are attached to form a carbonyl;

$R_6$ is selected from hydrogen, hydroxyl, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine;

$R_7$ is selected from hydrogen, hydroxyl, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine; or $R_6$ and $R_7$ combine together with the atoms to which they are attached form a substituted or unsubstituted $C_5$-$C_8$ cycloalkyl, a substituted or unsubstituted $C_5$-$C_8$ cycloalkenyl, or a substituted or unsubstituted $C_5$-$C_8$ heterocycle; and ---- represents a bond that is present or absent.

In some embodiments of Formula (I), the compound has a formula (I-A):

(I-A)

or a pharmaceutically acceptable derivative thereof;

wherein $R_1$, $R_2$, and $R_5$ are independently selected from hydrogen, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine;

$R_3$ and $R_4$ are independently, for each occurrence, selected from hydrogen, hydroxyl, substituted or unsubstituted $C_1$-$C_6$ alkyl, substituted or unsubstituted $C_1$-$C_6$ ester, or $R_3$ and $R_4$ combine together with the atom to which they are attached to form a carbonyl; and $R_8$ is selected from hydrogen, hydroxyl, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine.

In further embodiments of Formula (I), the compound has a formula (I-B):

(I-B)

or a pharmaceutically acceptable derivative thereof;

wherein $R_1$, $R_2$, and $R_5$ are independently selected from hydrogen, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine;

$R_3$ and $R_4$ are independently, for each occurrence, selected from hydrogen, hydroxyl, substituted or unsubstituted $C_1$-$C_6$ alkyl, substituted or unsubstituted $C_1$-$C_6$ ester, or $R_3$ and $R_4$ combine together with the atom to which they are attached to form a carbonyl;

$R_6$ is selected from hydroxyl, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine; and $R_7$ is selected from hydroxyl, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine.

In some embodiments of Formula (I), Formula (I-A), Formula (I-B), $R_6$ can be selected from substituted or unsubstituted $C_1$-$C_6$ alkyl. For example, $R_6$ can be selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle.

In some embodiments of Formula (I), Formula (I-A), Formula (I-B), $R_7$ can be selected from substituted or unsubstituted $C_1$-$C_6$ alkyl or substituted or unsubstituted $C_1$-$C_6$ ester. For example, $R_7$ can be selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle.

In some embodiments of Formula (I), Formula (I-A), Formula (I-B), $R_6$ can be selected from substituted or unsubstituted $C_1$-$C_6$ alkyl, and $R_7$ is selected from substituted or unsubstituted $C_1$-$C_6$ alkyl or substituted or unsubstituted $C_1$-$C_6$ ester.

In some embodiments of Formula (I), Formula (I-A), Formula (I-B), $R_1$ can be selected from $C_1$-$C_6$ alkyl, $C_1$-$C_6$ alkyl halide, $C_1$-$C_6$ alkoxy, $C_1$-$C_6$ ester, and $C_1$-$C_6$ alkylamine. For example, $R_1$ can be selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle.

In some embodiments of Formula (I), Formula (I-A), Formula (I-B), $R_2$ can be selected from $C_1$-$C_6$ alkyl, $C_1$-$C_6$ alkyl halide, $C_1$-$C_6$ alkoxy, $C_1$-$C_6$ ester, and $C_1$-$C_6$ alkylamine. For example, $R_2$ can be selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle.

In some embodiments of Formula (I), Formula (I-A), Formula (I-B), $R_5$ can be selected from $C_1$-$C_6$ alkyl, $C_1$-$C_6$ alkyl halide, $C_1$-$C_6$ alkoxy, $C_1$-$C_6$ ester, and $C_1$-$C_6$ alkylamine. For example, $R_5$ can be selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle.

In some embodiments of Formula (I), Formula (I-A), Formula (I-B), $R_1$, $R_2$, and $R_5$ are independently selected from $C_1$-$C_6$ alkyl, $C_1$-$C_6$ alkyl halide, $C_1$-$C_6$ alkoxy, $C_1$-$C_6$ ester, and $C_1$-$C_6$ alkylamine. For example, $R_1$, $R_2$, and $R_5$ can be independently selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle.

In some embodiments of Formula (I), Formula (I-A), Formula (I-B), at least one $R_3$ and $R_4$ combine together with the atom to which they are attached to form a carbonyl. In other embodiments of Formula (I), Formula (I-A), Formula (I-B), $R_3$ and $R_4$ can be independently, for each occurrence, selected from hydrogen or unsubstituted $C_1$-$C_6$ alkyl. For example, $R_3$ and $R_4$ can be hydrogen.

In some embodiments of Formula (I), Formula (I-A), Formula (I-B), $R_5$ can be selected from substituted or unsubstituted $C_1$-$C_6$ alkyl or substituted or unsubstituted $C_1$-$C_6$ ester. For example, $R_5$ can be selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle.

The compositions described herein can be a pharmaceutical composition comprising a therapeutically effective amount of a compound, or a pharmaceutically acceptable derivative thereof, and a pharmaceutically acceptable carrier, wherein the compound has a structure represented by Formula (II):

(II)

wherein $R_{1a}$, $R_{1b}$, $R_{2a}$, and $R_{10}$ are independently selected from hydrogen, hydroxyl, amine, halogen, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine;

$R_{3a}$ and $R_{4a}$ are independently selected from hydrogen, hydroxyl, substituted or unsubstituted $C_1$-$C_{10}$ alkyl, substituted or unsubstituted $C_1$-$C_{10}$ alkenyl, substituted or unsubstituted $C_1$-$C_{10}$ ester, or $R_{3a}$ and $R_{4a}$ combine together with the atoms to which they are attached to form a carbonyl;

$R_{7a}$ is selected from hydrogen, hydroxyl, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine;

$R_9$ and $R_{11}$ are independently selected from hydrogen, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine; and $R_{12}$ is selected from hydrogen, hydroxyl, amine, halogen, cyano, nitro, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine.

In some embodiments of Formula (II), the compound has a formula (II-A):

(II-A)

or a pharmaceutically acceptable derivative thereof;

wherein $R_{1a}$, $R_{1b}$, and $R_{10}$ are independently, for each occurrence, selected from hydrogen, hydroxyl, amine, halogen, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine;

$R_{4a}$ is selected from substituted or unsubstituted $C_1$-$C_{10}$ alkyl, substituted or unsubstituted $C_1$-$C_{10}$ alkenyl, or substituted or unsubstituted $C_1$-$C_{10}$ ester;

$R_{7a}$ is selected from hydrogen, hydroxyl, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine;

$R_9$ and $R_{11}$ are independently selected from hydrogen, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine; and $R_{12}$ is selected from hydrogen, hydroxyl, amine, halogen, cyano, nitro, substituted or unsubstituted $C_1$-$C_6$ alkyl, substituted or unsubstituted $C_1$-$C_6$ alkyl halide, substituted or unsubstituted $C_1$-$C_6$ alkoxy, substituted or unsubstituted $C_1$-$C_6$ ester, and substituted or unsubstituted $C_1$-$C_6$ alkylamine.

In some embodiments of Formula (II) and Formula (II-A), $R_{1a}$ is selected from hydroxyl, amine, halogen, $C_1$-$C_6$ alkoxy, and $C_1$-$C_6$ ester. For example, $R_{1a}$ can be selected from hydroxyl, and $C_1$-$C_6$ ester.

In some embodiments of Formula (II) and Formula (II-A), $R_{1b}$ is selected from hydroxyl, amine, halogen, $C_1$-$C_6$ alkoxy, and $C_1$-$C_6$ ester. For example, $R_{1b}$ can be selected from hydroxyl, and $C_1$-$C_6$ ester.

In some embodiments of Formula (II) and Formula (II-A), $R_{10}$ is selected from hydroxyl, amine, halogen, $C_1$-$C_6$ alkoxy, and $C_1$-$C_6$ ester. For example, $R_{10}$ can be selected from hydroxyl, and $C_1$-$C_6$ ester.

In some embodiments of Formula (II) and Formula (II-A), $R_{1a}$, $R_{1b}$, and $R_{10}$ are independently selected from hydroxyl, amine, halogen, $C_1$-$C_6$ alkoxy, and $C_1$-$C_6$ ester. For example, $R_{1a}$, $R_{1b}$, and $R_{10}$ can be selected from hydroxyl, and $C_1$-$C_6$ ester.

In some embodiments of Formula (II) and Formula (II-A), $R_{3a}$ can be selected from hydrogen, $C_1$-$C_6$ alkyl, $C_1$-$C_6$ alkyl halide, $C_1$-$C_6$ alkoxy, $C_1$-$C_6$ ester, and $C_1$-$C_6$ alkylamine. For example, $R_{3a}$ can be selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle.

In some embodiments of Formula (II) and Formula (II-A), $R_{4a}$ can be selected from hydrogen $C_1$-$C_6$ alkyl, $C_1$-$C_6$ alkyl halide, $C_1$-$C_6$ alkoxy, $C_1$-$C_6$ ester, and $C_1$-$C_6$ alkylamine. For example, $R_{4a}$ can be selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle.

In some embodiments of Formula (II) and Formula (II-A), $R_{3a}$ and $R_{4a}$ can be selected from hydrogen, $C_1$-$C_6$ alkyl, $C_1$-$C_6$ alkyl halide, $C_1$-$C_6$ alkoxy, $C_1$-$C_6$ ester, and $C_1$-$C_6$ alkylamine. For example, $R_{3a}$ and $R_{4a}$ can be selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle. In some instances, at least one of $R_{3a}$ and $R_{4a}$ is hydrogen.

In some embodiments of Formula (II) and Formula (II-A), $R_9$ can be selected from hydrogen, $C_1$-$C_6$ alkyl, $C_1$-$C_6$ alkyl halide, $C_1$-$C_6$ alkoxy, $C_1$-$C_6$ ester, and $C_1$-$C_6$ alkylamine. For example, $R_9$ can be selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle. $R_9$ can be selected from methyl, ethyl, or propyl.

In some embodiments of Formula (II) and Formula (II-A), $R_{11}$ can be selected from hydrogen, $C_1$-$C_6$ alkyl, $C_1$-$C_6$ alkyl halide, $C_1$-$C_6$ alkoxy, $C_1$-$C_6$ ester, and $C_1$-$C_6$ alkylamine. For example, $R_{11}$ can be selected from $C_1$-$C_6$ alkyl optionally substituted with carbonyl, hydroxyl, alkyl, alkoxy, nitro, nitrate ester, ester, alkyl halide, alkyl amine, aryl, heteroaryl, cycloalkyl, cycloalkenyl or heterocycle. $R_{11}$ can be selected from methyl, ethyl, or propyl.

In some embodiments of Formula (II) and Formula (II-A), $R_{12}$ can be selected from hydroxyl, amine, halogen, cyano, ester, and nitro. For example, $R_{12}$ can be hydroxyl.

When substituted, $R_1$ to $R_{12}$ can be independently substituted with carbonyl, halogen, cyano, hydroxyl, alkyl, alkoxy, nitro, nitrate ester, alkenyl, ester, alkyl halide, alkyl amine, aryl, heteroaryl, cycloalkyl, cycloalkenyl or heterocycle.

In some examples, the compound can be an alcyopterosin or a derivative thereof. For example, the compound can be alcyopterosin E, alcyopterosin G, alcyopterosin C, alcyopterosin O, alcyopterosin L, or a derivative thereof. In some examples, the compound can be an oxidised steroid such as Formula II described herein or a derivative thereof. In some embodiments of Formula (I) and Formula (II) described herein, the compound can have a structure:

, or a derivative thereof.

Compositions

The disclosed compounds can be used therapeutically in combination with a pharmaceutically acceptable carrier. The carrier would naturally be selected to minimize any degradation of the active ingredient and to minimize any adverse side effects in the subject, as would be well known to one of skill in the art.

The disclosed compounds may be in solution, suspension, incorporated into microparticles, liposomes, or cells, or formed into tablets, gels, or suppositories. Suitable carriers and their formulations are described in Remington: The Science and Practice of Pharmacy ($22^{nd}$ ed.) eds. Lloyd V. Allen, Jr., et al., Pharmaceutical Press, 2012. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. Pharmaceutical compositions may include carriers, thickeners, diluents, buffers, preservatives, surface active agents and the like. Pharmaceutical compositions may also include one or more additional active ingredients such as antimicrobial agents, anti-inflammatory agents, anesthetics, and the like.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 2002/0035243 also describes compositions for transporting biological moieties across cell membranes for intracellular delivery. Compounds can also be incorporated into polymers, examples of which include poly (D-L lactide-co-glycolide) polymer; poly[bis(p-carboxyphenoxy) propane:sebacic acid] in a 20:80 molar ratio (as used in GLIADEL); chondroitin; chitin; and chitosan.

For the treatment of infections, the compounds disclosed herein can be administered to a patient in need of treatment in combination with other antimicrobial substances to treat the infection. These other substances or treatments can be given at the same as or at different times from the compounds disclosed herein.

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to treat an infection site. Compounds and agents disclosed herein can be applied directly to the infection site. Preferably, the compounds and agents are applied to the infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Kits

Kits for practicing the methods of the invention are further provided. By "kit" is intended any manufacture (e.g., a package or a container) comprising at least one reagent, e.g., anyone of the compounds described herein. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more antimicrobial agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Methods

The present disclosure provides methods for treating a subject with a condition (e.g., an infection) or disease. The method can include administering to the subject a therapeutically effective amount of a compound having a formula described herein or a pharmaceutically acceptable derivative thereof.

The compounds and compositions disclosed herein can be used individually or in combination (e.g., in the same composition or separately) with other antimicrobials to treat one or multiple types and/or strains of microorganisms such as bacteria, protozoa, and the like, which can include exposing the microorganisms to an appropriate amount of the composition to achieve the desired goal, by administering a therapeutically effective amount of the composition to the subject (e.g., human), or the like. Embodiments of the present disclose can be used as a broad spectrum antimicrobial (e.g., broad spectrum antibiotic, broad spectrum antiprotozoal, and the like). In an embodiment, compositions of the present disclosure can be used to treat subjects (e.g. humans) having infections caused by protozoa such as *Leishmania*, *Plasmodium*, and *Toxoplasma*, or a combination thereof by administering a therapeutically effective amount of the composition. In an embodiment, compositions of the present disclosure can be used to treat subjects having infections caused by bacteria such as: *Enterococcus faecium*, *Staphylococcus aureus*, *Klebsiella pneumoniae*, *Acinetobacter baumannii*, *Pseudomonas aeruginosa*, *Enterobacter cloacae*, or combinations thereof by administering a therapeutically effective amount of the composition.

In some embodiments, the infectious disease is a parasitic disease related to leishmaniasis and related diseases including, but not limited to malaria, human African trypanomiasis, babesiosis, Chagas disease, microsporidiosis, pneumocystosis, primary ameobic meningoenchephalitis, and toxoplasmosis. In certain embodiments, the parasitic disease can be caused by a Leishmaniasis sp. such as *Leishmania donovani*, *Leishmannia brasiliensis*, *Leishmania mexicana*, *Leishmania amazonensis*, *Leishmania aethiopica*, *Leishmania major*, *Leishmania chagasi*, *Leishmania panamensis*, *Leishmania infantum*, and *Leishmania tropica*.

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lungcancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

EXAMPLES

Example 1: New Alcyopterosins and Steroids

Marine invertebrates from *Antarctica* have been investigated for their potential natural product chemistry. Often sessile, these organisms must develop chemical protective mechanisms to survive and defend themselves against predators. The biodiversity of these organisms is of particular interest due to the extremely low temperatures and the circumpolar current around the Antarctic continent serving as an ecological isolating shield. The chemodiversity that emanates from these organisms can be a significant source of chemistry to be further developed into new drugs. The chemical investigation of an undescribed *Gersemia* sp. Antarctic coral has led to the isolation of two different kinds of bioactive compounds. After lyophilization of the organism, two different extractions were performed: the first one used a methylene chloride: methanol (1:1) solvent mixture, and the second one used methylene chloride only as solvent in a Soxhlet extraction. After a partition followed by normal phase Medium Pressure Liquid Chromatography, stages of normal phase and reverse phase High Performance Liquid Chromatography purifications were performed and revealed two kinds of new bioactive compounds: new acetylated sesquiterpenoids with alcyopterosin scaffolds from the first process and new acetylated steroids from the second. One and two-dimensional nuclear magnetic resonance, mass spectrometry, X-ray crystallography, and circular dichroism were the methods performed to elucidate and confirm the structures. Furthermore, biological testing against *Leishmania* sp. and ESKAPE pathogens, Zika virus, *Clostridium difficile*, and HeLa cancer cells were performed.

Results

Figure 1:
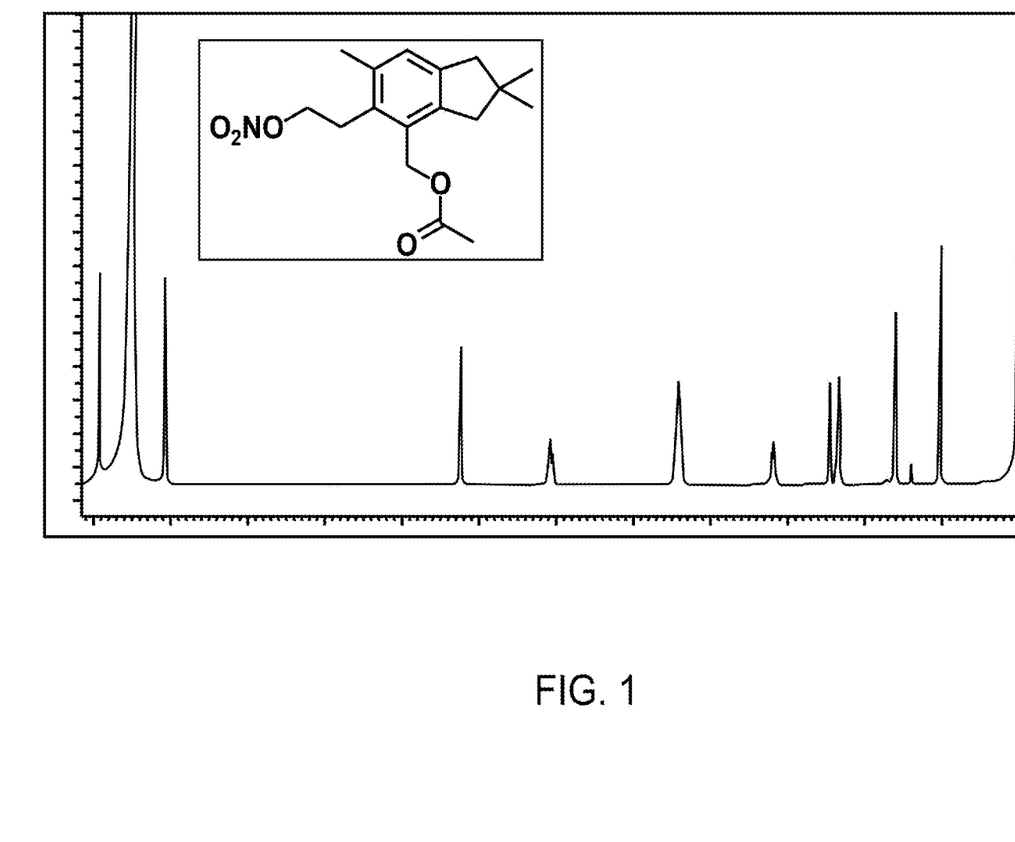
FIG. 1 shows proton NMR spectra of two alcyopterosins.
Figure 2:
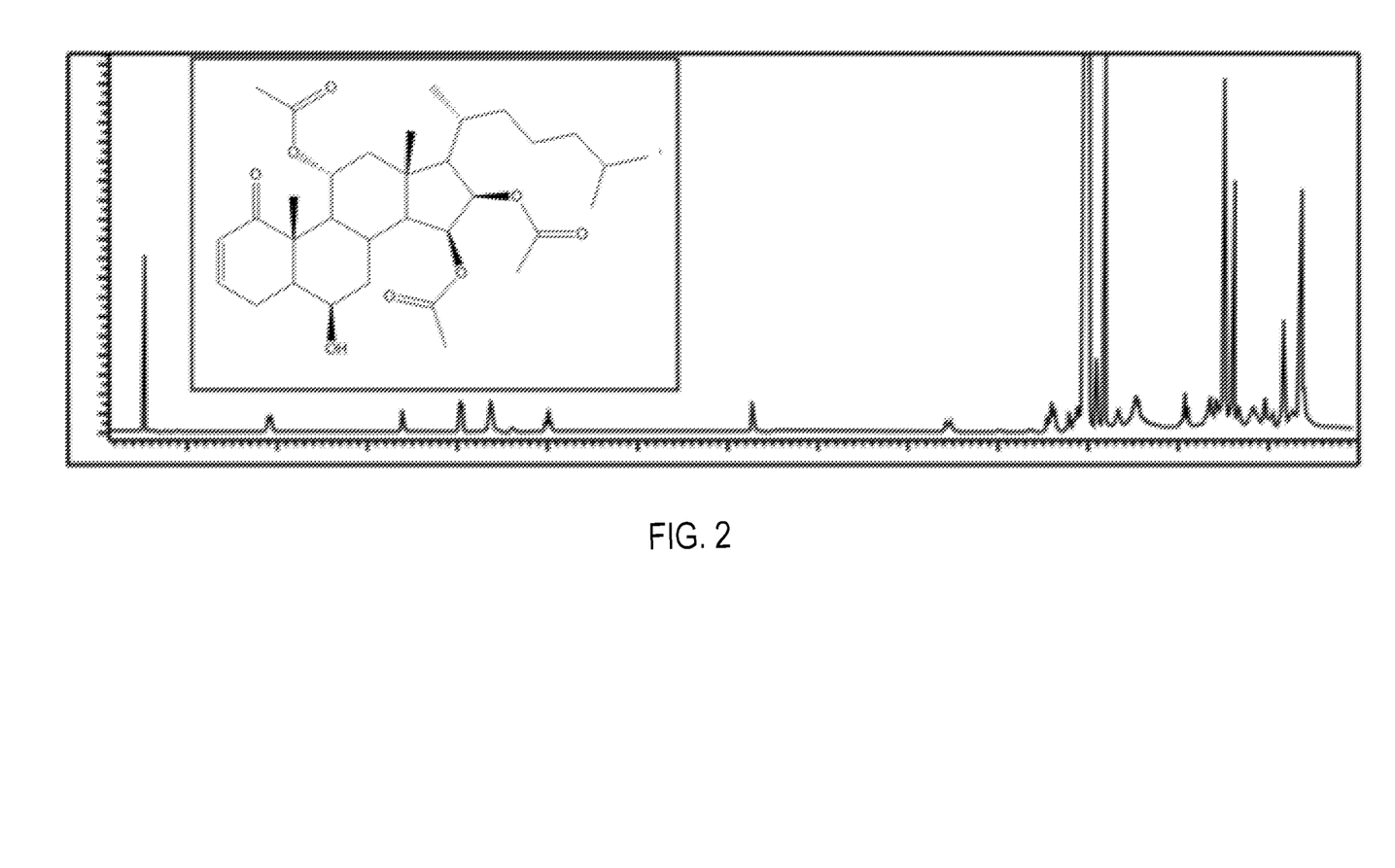
FIG. 2 shows proton NMR spectra of an oxidized steroid.
Figure 3:
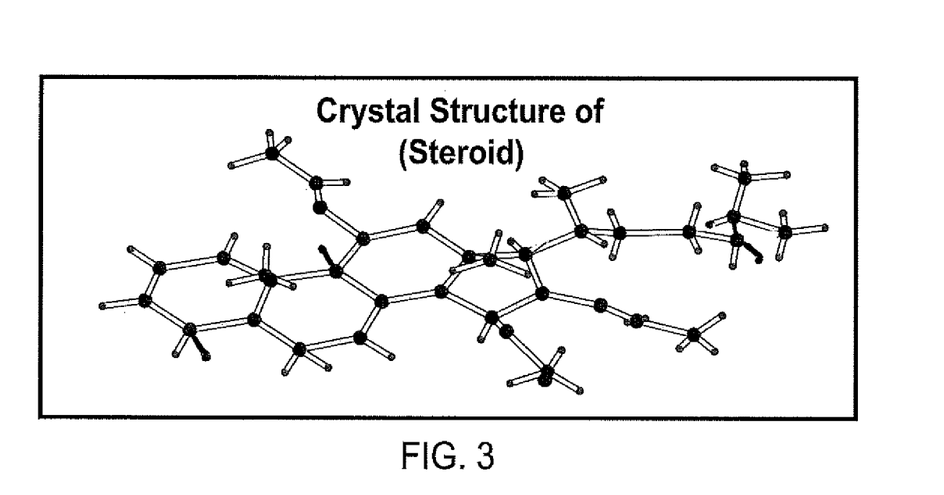
FIG. 3 shows the crystal structure of oxidized steroid from FIG. 2.
Figure 4:
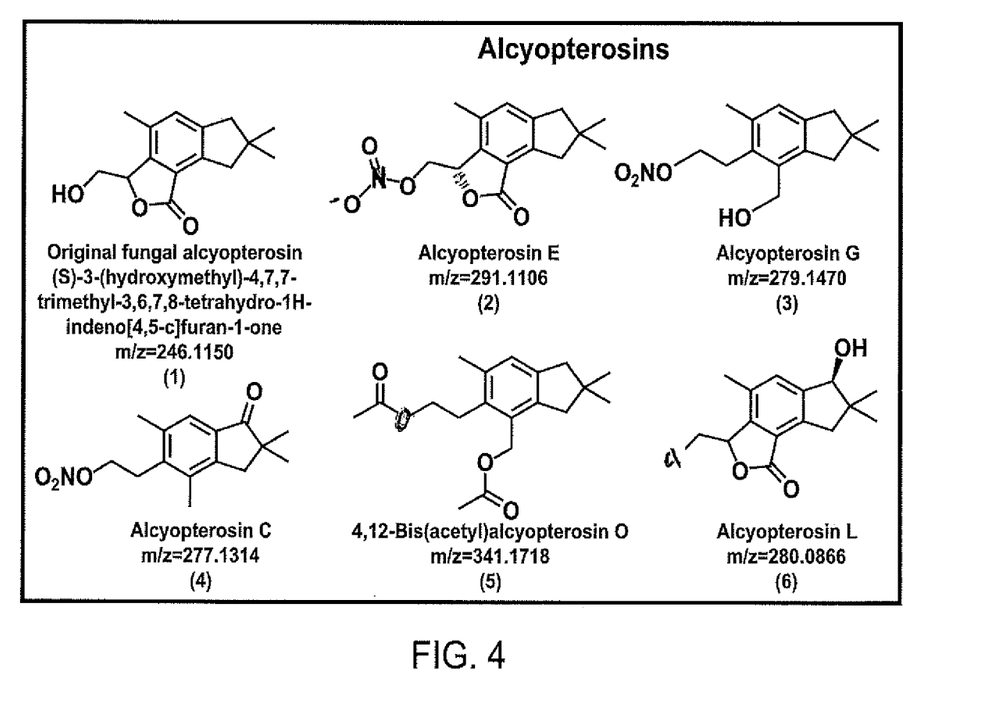
FIG. 4 shows chemical structures several alcyopterosins.

Isolated Compounds:

Compounds shown in FIGS. 2 and 3 were isolated from the Antarctic coral.

Circular Dichroism:

The absolute stereochemistry of the carbon bearing acetate moiety is assessed by comparison of experimental and calculated circular dichroism values. The computational study calculated values for both R and S enantiomers. The calculated value matching the sign of the experimental trend confirmed the R stereochemistry for ACDL-12.

Bioassay:

Table 1 details the bioactivity of two Alcyopterosins and ACDL-21.

TABLE 1

| Assay | *Leishmania donovani* | Leishmaniasis |
|---|---|---|
| Fungal Alcyopterosin (1) | IC50 = 7.0 µm | |
| Alcyopterosin E (2) | IC50 = 3.1 µm | |
| ACDL-21 | | IC50 = 1.5 µm |

Summary:

New Alcyopterosins and steroids were isolated from an Antarctic coral and their bioactivities were described.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative materials and method steps disclosed herein are specifically described, other combinations of the materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms.

What is claimed is:

1. A pharmaceutical composition comprising a therapeutically effective amount of a compound, and a pharmaceutically acceptable carrier to treat an infection, wherein the compound has a structure represented by formula (I) or formula (II):

wherein $R_1$, $R_2$, and $R_5$ are independently selected from the group consisting of hydrogen, unsubstituted $C_1$-$C_6$ alkyl, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine;

$R_{1a}$ and $R_{10}$ are independently selected from the group consisting of hydroxyl, amine, halogen, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine;

$R_{1b}$ and $R_{2a}$ are independently selected from the group consisting of hydrogen, hydroxyl, amine, halogen, unsubstituted $C_1$-$C_6$ alkyl, unsubstituted $C_1$-$C_6$ alkyl halide, unsubstituted $C_1$-$C_6$ alkoxy, unsubstituted —OC(O)$C_2$-$C_5$, unsubstituted —C(O)OC$_1$-$C_5$, and unsubstituted $C_1$-$C_6$ alkylamine;

$R_3$ and $R_4$ are independently, for each occurrence, selected from the group consisting of hydrogen, unsubstituted $C_1$-$C_6$ alkyl, unsubstituted $C_1$-$C_6$ ester, or $R_3$ and $R_4$ combine together with the atom to which they are attached to form a carbonyl;

$R_{3a}$ and $R_{4a}$ are independently selected from the group consisting of hydrogen, hydroxyl, unsubstituted $C_1$-$C_{10}$ alkyl, unsubstituted $C_1$-$C_{10}$ alkenyl, unsubstituted $C_1$-$C_{10}$ ester, or $R_{3a}$ and $R_{4a}$ combine together with the atoms to which they are attached to form a carbonyl;

$R_6$ is selected from the group consisting of hydrogen, hydroxyl, unsubstituted $C_1$-$C_6$ alkyl, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine;

$R_7$ is selected from the group consisting of hydrogen, hydroxyl, unsubstituted $C_2$-$C_6$ alkyl, unsubstituted $C_1$-$C_6$ alkyl halide, unsubstituted $C_1$-$C_6$ alkoxy, unsubstituted —OC(O)$C_2$-$C_5$, unsubstituted —C(O)OC$_1$-$C_5$, and unsubstituted $C_1$-$C_6$ alkylamine;

$R_{7a}$ is selected from the group consisting of hydrogen, hydroxyl, unsubstituted $C_1$-$C_6$ alkyl, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine; or

$R_6$ and $R_7$ combine together with the atoms to which they are attached form a substituted $C_5$-$C_8$ cycloalkyl, a substituted $C_5$-$C_8$ cycloalkenyl, or a substituted $C_5$-$C_8$ heterocycle, wherein the substituents include carbonyl and one or more of hydroxyl, unsubstituted $C_2$-$C_6$ alkyl, unsubstituted $C_1$-$C_6$ alkoxy, unsubstituted $C_1$-$C_6$ ester, and unsubstituted $C_1$-$C_6$ alkylamine;

$R_9$ and $R_{11}$ are independently selected from the group consisting of hydrogen, unsubstituted $C_1$-$C_6$ alkyl, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine; and $R_{12}$ is selected from the group consisting of hydrogen, hydroxyl, amine, halogen, cyano, nitro, unsubstituted $C_1$-$C_6$ alkyl, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine; and represents a bond that is present or absent.

2. The pharmaceutical composition of claim 1, wherein the compound has a formula (I-A):

(I-A)

wherein $R_8$ is selected from the group consisting of hydroxyl, unsubstituted $C_2$-$C_6$ alkyl, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine.

3. The pharmaceutical composition of claim 1, wherein the compound has a formula (I-B):

(I-B)

wherein $R_6$ is selected from the group consisting of hydroxyl, unsubstituted $C_1$-$C_6$ alkyl, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine;

$R_7$ is selected from the group consisting of hydroxyl, unsubstituted $C_2$-$C_6$ alkyl, unsubstituted $C_1$-$C_6$ alkyl halide, unsubstituted $C_1$-$C_6$ alkoxy, unsubstituted —OC(O)$C_2$-$C_5$, unsubstituted —C(O)OC$_1$-$C_5$, and unsubstituted $C_1$-$C_6$ alkylamine.

4. The pharmaceutical composition of claim 3, wherein $R_6$ is selected from unsubstituted $C_1$-$C_6$ alkyl.

5. The pharmaceutical composition of claim 1, wherein $R_1$, $R_2$, and $R_5$ are independently selected from the group consisting of unsubstituted $C_1$-$C_6$ alkyl and unsubstituted $C_1$-$C_6$ alkoxy.

6. The pharmaceutical composition of claim 1, wherein the compound has a structure represented by formula (II-A):

(II-A)

wherein $R_{1a}$ and $R_{10}$ are independently, for each occurrence, selected from the group consisting of hydroxyl, amine, halogen, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine;

$R_{4a}$ is selected from the group consisting of unsubstituted $C_1$-$C_{10}$ alkyl, unsubstituted $C_1$-$C_{10}$ alkenyl, or unsubstituted $C_1$-$C_{10}$ ester.

7. The pharmaceutical composition of claim 1, wherein $R_{1a}$, $R_{1b}$, and $R_{10}$ are independently selected from the group consisting of hydroxyl, amine, halogen, $C_1$-$C_6$ alkoxy, OC(O)$C_2$-$C_5$, and —C(O)OC$_1$-$C_5$.

8. The pharmaceutical composition of claim 1, wherein $R_{12}$ is selected from the group consisting of hydroxyl, amine, halogen, cyano, and nitro.

9. A pharmaceutical composition to treat an infection comprising a therapeutically effective amount of a compound according to claim 1 or a compound having a structure below, and a pharmaceutically acceptable carrier selected from the group consisting of a cream, gel, liposome, nanoparticle, ointment, a tablet, capsule, or suppository:

(I-A)

10. A method of treating an infection comprising: delivering to a subject in need thereof, a pharmaceutical composition according to claim 1, wherein the pharmaceutical composition comprises a therapeutically effective amount of a compound having a structure represented by formula (I) or formula (II), and a pharmaceutically acceptable carrier, to treat the infection, wherein the infection is a parasitic infection associated with a *Leishmania* sp.

11. The method of claim 10, wherein the compound has a formula (I-A):

wherein $R_8$ is selected from the group consisting of hydroxyl, unsubstituted $C_2$-$C_6$ alkyl, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine.

12. The method of claim 10, wherein the compound has a formula (I-B):

(I-B)

wherein $R_6$ is selected from the group consisting of hydroxyl, unsubstituted $C_1$-$C_6$ alkyl, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine;

$R_7$ is selected from the group consisting of hydroxyl, unsubstituted $C_2$-$C_6$ alkyl, unsubstituted $C_1$-$C_6$ alkyl halide, unsubstituted $C_1$-$C_6$ alkoxy, unsubstituted $OC(O)C_2$-$C_5$, unsubstituted —$C(O)OC_1$-$C_5$, and unsubstituted $C_1$-$C_6$ alkylamine.

13. The method of claim 10, wherein $R_6$ is selected from unsubstituted $C_1$-$C_6$ alkyl.

14. The method of claim 10, wherein $R_1$, $R_2$, and $R_5$ are independently selected from the group consisting of unsubstituted $C_1$-$C_6$ alkyl, unsubstituted $C_1$-$C_6$ alkoxy.

15. The method of claim 10, wherein the compound has a structure represented by formula (II-A):

(II-A)

wherein $R_{1a}$ and $R_{10}$ are independently, for each occurrence, selected from the group consisting of hydroxyl, amine, halogen, unsubstituted $C_1$-$C_6$ alkyl halide, unsubstituted $C_1$-$C_6$ alkoxy, unsubstituted $C_1$-$C_6$ ester, and unsubstituted $C_1$-$C_6$ alkylamine;

$R_{4a}$ is selected from the group consisting of unsubstituted $C_1$-$C_{10}$ alkyl, unsubstituted $C_1$-$C_{10}$ alkenyl, or unsubstituted $C_1$-$C_{10}$ ester.

16. A method of treating an infection comprising: delivering to a subject in need thereof, a pharmaceutical composition according to claim 9.

17. The method of claim 10, wherein the parasitic infection is associated with *Leishmania donovani*.

18. The method of claim 10, wherein the subject is a mammal.

* * * * *